United States Patent [19]

Yamada et al.

[11] Patent Number: 5,250,434
[45] Date of Patent: Oct. 5, 1993

[54] MICROORGANISMS FOR PRODUCTION OF GLUTAMIC ACID

[75] Inventors: Kazuhiko Yamada; Akira Seto, both of Kawasaki, Japan

[73] Assignee: Ajinomoto Co., Inc., Tokyo, Japan

[21] Appl. No.: 702,111

[22] Filed: May 16, 1991

Related U.S. Application Data

[63] Continuation of Ser. No. 160,845, Feb. 26, 1988, abandoned.

[30] Foreign Application Priority Data

Mar. 27, 1987 [JP] Japan .................. 62-075727

[51] Int. Cl.$^5$ .................. C12N 1/20; C12P 13/14
[52] U.S. Cl. .................. 435/252.1; 435/843; 435/110
[58] Field of Search .................. 635/110, 252.1, 863, 635/822

[56] References Cited

U.S. PATENT DOCUMENTS 3,338,793 8/1967 Tamamoto et al. .................. 435/110
3,355,359 11/1967 Goto et al. .................. 435/110

FOREIGN PATENT DOCUMENTS 1268180 11/1985 Japan .................. 435/110

OTHER PUBLICATIONS

Goodfellow et al, "The Biology of the Actino Mycetes," Academic Press 1984, pp. 77–79.
Chemical Abstracts, vol. 80, No. 13, Apr. 1, 1974, p. 221, resume No 69157a, Columbus Ohio, US; JP-A-73 27 477 (Kyowa Fermentation Industry Co., Ltd.) Aug. 22, 1973.
Patent Abstracts of Japan, vol. 11, No. 242 (C-438) [2689], 7 aout 1987; & JP-A-62 48 393 (Ajinomoto Co. Inc.) Mar. 3, 1987.

*Primary Examiner*—Irene Marx
*Attorney, Agent, or Firm*—Oblon, Spivak, McClelland, Maier & Neustadt

[57] ABSTRACT

Novel bacteria identified as effective in glutamic acid production through fermentation chemistry conducted at temperatures above 42° C.

1 Claim, No Drawings

MICROORGANISMS FOR PRODUCTION OF GLUTAMIC ACID

This application is a continuation of application Ser. No. 07/160,845, filed on Feb. 26, 1988, now abandoned.

BACKGROUND OF THE INVENTION

1. Field of the Invention

The present invention relates to a novel microorganism capable of accumulating a marked amount of glutamic acid by fermentation and a method for producing the desired product by culturing the microorganism.

2. Background of the Prior Art

In a method which comprises accumulating a marked amount of glutamic acid and collecting the same, namely, production of glutamic acid fermentation in an industrial scale, microorganisms capable of accumulating a marked amount of glutamic acid in medium, so called glutamic acid-producing bacteria, are cultured in a fermentation tank using an appropriate medium under suitably controlled culture conditions such as pH, temperature, amount of dissolved oxygen, etc. Many reports have been made on classification of glutamic acid-producing bacteria hitherto known and, for example, the following publications are given.

1. Kinoshita et al., Amino Acids, 2, 42 (1960) (hereafter referred to as Publication (1))
2. Okumura et al., J. Agr. Chem. Soc. Japan, 36, 141 (1962) (hereafter referred to as Publication (2))
3. Takayama et al., J. Agr. Chem. Soc. Japan, 39, 328 (1965) (hereafter referred to as Publication (3))
4. Takayama et al., J. Agr. Chem. Soc. Japan, 39, 335 (1965) (hereafter referred to as Publication (4))
5. Takayama et al., J. Agr. Chem. Soc. Japan, 39, 342 (1965) (hereafter referred to as Publication (5))
6. Komagata et al., J. Gen. Appl. Microbiol., 15, 243 (1969) (hereafter referred to as Publication (6))
7. Yamada et al., J. Gen. Appl. Microbiol., 16, 103 (1970) (hereafter referred to as Publication (7))
8. Yamada et al., J. Gen. Appl. Microbiol., 16, 215 (1970) (hereafter referred to as Publication (8))
9. Yamada et al., J. Gen. Appl. Microbiol., 18, 399 (1972) (hereafter referred to as Publication (9))
10. Yamada et al., J. Gen. Appl. Microbiol., 18, 417 (1972) (hereafter referred to as Publication (10))

In these reports, the glutamic acid-producing bacteria are not necessarily defined strictly to be bacteria capable of accumulating a marked amount of glutamic acid in medium. However, as a measure for the production amount, the glutamic acid-producing bacteria are reasonably interpreted to refer to industrially utilizable microorganisms capable of accumulating at least 30 g/l of glutamic acid in a medium in a yield of at least 30% based on glucose, as described in Publication (1).

These known glutamic acid-producing bacteria are all aerobic, gram-positive and non-sporeforming rods and classified in a bacterial group named coryneform bacteria. In addition, there are known facts regarding morphological properties and physiological and biological properties including that they are capable of accumulating a marked amount of glutamic acid in a medium, are biotin auxotrophic, contain mesodiaminopimelic acid in cell walls and have GC content of about 55% in DNA are similar to each other, etc. From these facts, it is widely admitted that known microorganisms called glutamic acid-producing bacteria are taxonomically akin to each other. In spite of the fact that they are considered to be microorganisms akin to each other, known glutamic acid-producing bacteria are identified to be in different genera such as the genus Brevibacterium, the genus Corynebacterium, the genus Microbacterium, etc. A major cause for this phenomenon of giving various classifications is believed to be earlier practices in identification which was made, inter alia, on a different classification system and a classification standard of the newest version of Bergey's Mannual of Determinative Bacteriology at that time, which is the most authoritative identification book for bacteria in the world, a difference in an identifier's weight on classification standard, etc. Further Kinoshita et al. (Publication (1)) made taxonomical research on approximately 20 glutamic acid-producing bacteria and using common properties possessed by these bacteria as the classification standard, proposed to create the genus of glutamic acid-producing bacteria. However, this proposal has not been adopted widely to date.

In production of glutamic acid by fermentation in an industrial scale, the aforesaid glutamic acid-producing bacteria are cultured in a medium containing components such as glucose, sucrose, acetic acid, etc. under aerobic conditions, using ammonia, urea, ammonium sulfate, etc. as nitrogen sources to accumulate a marked amount of glutamic acid in a medium. The amount of glutamic acid to be accumulated varies depending upon composition of medium, pH for incubation, culture temperature, amount of dissolved oxygen, means for secreting the glutamic acid produced in cells into medium, etc. However, by setting forth these factors in optimum ranges, glutamic acid can be accumulated in a yield of 30% or more based on glucose in a concentration of accumulated glutamic acid of 30 g/l or more.

Glutamic acid has been industrially produced by the fermentation method described above not only in Japan but also in many other countries. In the industrial production, one of the most important factors is high production rates. The present invention is to provide a highly economical technique for producing glutamic acid by fermentation in an industrial scale.

SUMMARY OF THE INVENTION

In the industrial production of glutamic acid by fermentation, there are some technical standards to measure improvement from an economical standpoint. For example, these factors are an increase in yield based on glucose, an increase in concentration of glutamic acid accumulated, shortening of incubation time, etc. An additional important factor is elevation of the incubation temperature. Incubation is carried out at an optimum temperature for fermentation of glutamic acid; in the case of using conventional glutamic acid-producing bacteria, this temperature is generally at 31° to 32° C. When incubation is initiated, fermentation heat generates so that if the system is allowed to stand as it is, a temperature of the culture solution will increase so that production of glutamic acid will be markedly reduced. In order to maintain the temperature of the culture solution in an optimum range, it is necessary to set a heat exchanger in a fermenter and recycle chilled water to the exchanger. In order to obtain chilled water, a freezer must be used but because of a vast amount of the fermentation heat generated, the electric energy consumed by the freezer is also large. Accordingly, if it is possible to elevate the incubation temperature in fermentation of glutamic acid higher than the conventional temperature, the burden of cooling can be reduced thereby to improve the industrial production from an economical viewpoint.

As a result of various investigations to solve the problem described above, the present inventors have found a novel microorganism capable of producing glutamic acid equal to conventional glutamic acid-producing bacteria (yield of 30% or more based on glucose, amount of accumulated glutamic acid of 30 g/l or more) and capable of accumulating a marked amount of glutamic acid in a high temperature region—for example, 43° C. at which conventional glutamic acid-producing bacteria do not grow and fermentation of glutamic acid is impossible. These microorganisms are grown at 45° C. in which conventional glutamic acid-producing bacteria cannot grow and the inventors, have found conditions for accumulating a marked amount of glutamic acid in a medium by glutamic acid fermentation, using the microorganism and have thus come to the present invention.

DETAILED DESCRIPTION OF THE INVENTION

With respect to the growth temperature of conventional glutamic acid-producing bacteria, the growth temperature is a property common to glutamic acid-producing bacteria in any report, as far as it is mentioned in the reports referred to above. Namely, it is reported in Publication (1) that glutamic acid-producing bacteria grow well at 28° to 37° C. In Publication (2), the bacteria grow well at 30° to 37° C. but many bacteria hardly grow at 42° C. It is also reported in Publication (4) that the optimum growth temperature is 25° to 37° C. but bacteria hardly grow at 42° C. It is reported in Publication (9) that no bacteria grow at 42° C. Even conceded that methods and standard for judging growth may be different in the respective publications, it is assumed that the highest growth temperature of conventional glutamic acid-producing bacteria would be about 42° C. The present inventors have determined the highest growth temperature of each of 20 strains shown in Table 1 which are almost all bacterial strains accessible from known bacteria deemed to be glutamic acid-producing bacteria, by two methods, i.e., a shake liquid thermostat method using nutrient broth as a medium, and by plate culture with a high accuracy gaseous thermostat using nutrient agar as a medium. As a result, no growth of the strains tested was noted at 42° C. at all by any of liquid culture and plate culture. It has thus been judged that the highest growth temperature of conventional glutamic acid-producing bacteria was below 42° C.

[Table 1] Known Glutamic Acid-Producing Bacteria Measured on the Highest Growth Temperature and Temperature Resistance

| | |
|---|---|
| *Brevibacterium ammoniagenes* | ATCC 13745 |
| *Brevibacterium divaricatum* | NRRL B2312 |
| *Brevibacterium flavum* | ATCC 13826 |
| *Brevibacterium flavum* | ATCC 14067 |
| *Brevibacterium glutamigenes* | ATCC 13747 |
| *Brevibacterium immariophilum* | ATCC 14068 |
| *Brevibacterium lactofermentum* | ATCC 13869 |
| *Brevibacterium roseum* | ATCC 13825 |
| *Brevibacterium saccharolyticum* | ATCC 14066 |
| *Brevibacterium taipei* | ATCC 13744 |
| *Brevibacterium thiogenitalis* | ATCC 19240 |
| *Corynebacterium acetoacidophilum* | ATCC 13870 |
| *Corynebacterium callunae* | NRRL B2244 |
| *Corynebacterium glutamicum* | ATCC 13032 |
| *Corynebacterium glutamicum* | ATCC 13761 |
| *Corynebacterium herculis* | ATCC 13868 |
| *Corynebacterium lilium* | NRRL B2243 |
| *Corynebacterium melassecola* | ATCC 17965 |
| *Corynebacterium sp.* | ATCC 14747 |
| *Microbacterium ammoniaphilum* | ATCC 15354 |

On the assumption that in order to perform glutamic acid fermentation in a temperature range higher than conventional incubation temperatures, microorganisms having a growth temperature maximum higher than that of conventional glutamic acid-producing bacteria would be required, the present inventors isolated microorganisms that grow at 43° C. from various samples in the natural world as sources for isolation and made a survey of strains capable of accumulating a marked amount of glutamic acid in medium and acquired 14 strains from different sources for isolation of the microorganisms. As a result of assay and identification of bacteriological properties of these strains, it has been judged that the isolated strains are akin to each other and classified in the same species. Bacteriological properties of four representative strains (Strain Nos. AJ 12308, AJ 12309, AJ 12310 and AJ 12340) are described below.

| | AJ 12308 | AJ 12309 | AJ 12310 | AJ 12340 |
|---|---|---|---|---|
| Morphological characteristics: | | | | |
| (1) Shape and size of cell | rod of (0.7–1.0) × (1.0–4.0)) round at both ends of cells; V-shaped arrangement based on snapping division is observed. | same as in the left column | same as in the left column | same as in the left column |
| (2) Pleomorphism | No pleomorphism is noted but depending upon period of culture, long rod cells, cystite cells and rudimentary branching cells are rarely noted. | same as in the left column | same as in the left column | same as in the left column |
| (3) Motility | none | same as in the left column | same as in the left column | same as in the left column |
| (4) Spore formation | none | same as in the left column | same as in the left column | same as in the left column |

-continued

|  | AJ 12308 | AJ 12309 | AJ 12310 | AJ 12340 |
|---|---|---|---|---|
| (5) Gram staining | positive | same as in the left column | same as in the left column | same as in the left column |
| (6) Acid fast staining | negative | same as in the left column | same as in the left column | same as in the left column |
| Cultural characteristics: | | | | |
| (1) Nutrient-agar plate culture | abundant or moderate growth; colonies are round, smooth, entire, convex, glistening, opaque or translucent, dull yellow and butyrous. | same as in the left column | same as in the left column | abundant or moderate growth; colonies are round, smooth lustrous, opaque or translucent, dull yellow and flake-like. |
| (2) Nutrient-agar slant culture | abundant or moderate growth; colonies are filiform, glistening and dull yellow. | same as in the left column | same as in the left column | same as in the left column |
| (3) Nutrient broth | moderate growth; almost uniformly turbid but some cells precipitate. | same as in the left column | same as in the left column | moderate growth; cells tend to gather and also precipitate. |
| (4) Nutrient-gelatin stab culture | moderate growth; non liquefaction | same as in the left column | same as in the left column | same as in the left column |
| (5) Litmus milk | made very weakly alkaline; neither liquefaction nor coagulation is noted. | same as in the left column | same as in the left column | same as in the left column |
| Physiological and biological characteristics: | | | | |
| (1) Reduction of nitrates | reduced | same as in the left column | same as in the left column | same as in the left column |
| (2) Denitrification | negative | same as in the left column | same as in the left column | same as in the left column |
| (3) MR test | negative or weakly positive | negative | negative or weakly positive | positive |
| (4) VP test | positive | negative | positive | negative |
| (5) Indole formation | negative | same as in the left column | same as in the left column | same as in the left column |
| (6) Formation of hydrogen sulfide | positive | same as in the left column | same as in the left column | same as in the left column |
| (7) Hydrolysis of starch | negative | same as in the left column | same as in the left column | same as in the left column |
| (8) Utilization of citrates | It does not grow in Koser's medium but grows in Christensen's medium to render the medium alkaline. | same as in the left column | same as in the left column | same as in the left column |
| (9) Utilization of inorganic nitrogen | It does not utilize nitrates, but utilize ammonium salt. | same as in the left column | same as in the left column | same as in the left column |
| (10) Formation of pigment | No extracellular formation of pigment. | same as in the left column | same as in the left column | same as in the left column |

-continued

| | AJ 12308 | AJ 12309 | AJ 12310 | AJ 12340 |
|---|---|---|---|---|
| (11) Urease test | negative or weakly positive | negative | negative or weakly positive | positive |
| (12) Oxidase | negative | same as in the left column | same as in the left column | same as in the left column |
| (13) Catalase | positive | same as in the left column | same as in the left column | same as in the left column |
| (14) Growth range | It grows well at pH 7-9.5; grows well at 25-45° C.; Slight growth is noted at 46° C. | same as in the left column | same as in the left column | It grows well at pH 7-9.5; grows well at 25-44° C.; Slight growth is noted at 45° C. |
| (15) Behavior to | aerobic or facultative anaerobic | same as in the left column | same as in the left column | same as in the left column |
| (16) O-F test (glucose) | It grows fermentatively to produce acid. | same as in the left column | same as in the left column | same as in the left column |
| (17) Acid formation from sugars: | | | | |
| (1) L-Arabinose | negative | negative | negative | negative |
| (2) D-Xylol | negative | negative | negative | negative |
| (3) D-Glucose | positive | positive | positive | positive |
| (4) D-Mannose | positive | positive | positive | positive |
| (5) D-Fructose | positive | positive | positive | positive |
| (6) D-galactose | negative | negative | negative | negative |
| (7) Maltose | positive | positive | positive | negative |
| (8) Sucrose | positive | positive | negative | positive |
| (9) Lactose | negative | negative | negative | negative |
| (10) Trehalose | negative | negative | positive | negative |
| (11) D-Sorbitol | negative | negative | negative | negative |
| (12) D-Mannitol | negative | negative | negative | positive |
| (13) Inositol | negative | negative | negative | positive |
| (14) Glycerine | negative | negative | negative | negative |
| (15) Starch | negative | negative | negative | negative |
| Other characteristics: | | | | |
| (1) Temperature resistance | It survives in skim milk at 60° -10 minutes by capillary method; It is dead at 65° C. for 10 minutes. | It survives in skim milk at 55° C. for 10 minutes by capillary method; it is dead at 60° C. for 10 min. | It survives in skim milk at 60° C. for 10 minutes by capillary method it is dead at 65° C. for 10 min. | It survives in skim milk at 55° C.-10 minutes by capillary method; it is dead at 60° C. for 10 minutes. |
| (2) Resistance to sodium chloride | It grows in 5% salt-containing medium. | same as in the left column | same as in the left column | same as in the left column |
| (3) Auxotrophy | It requires biotin for growth. | same as in the left column | same as in the left column | same as in the left column |
| (4) Base composition of DNA (Tm method) | 60.2% GC | 59.5% GC | 59.0% GC | 56.8% GC |
| (5) Dibasic amino acid contained in cell wall | mesodiaminopimelic acid | same as in the left column | same as in the left column | same as in the left column |
| (6) Source for isolation | fruit | vegetable soil | fruit | |

As shown above, these bacterial strains (hereafter referred to as the bacteria of the present invention) are all gram-positive, non-sporeforming rods which grow aerobically and therefore, belong to coryneform bacteria group. In addition, the bacteria of the present invention have characteristics that mode of cell division is of snapping type, dibasic amino acid contained in cell wall is mesodiaminopimelic acid, they are osmosis-resistant bacteria capable of growing in 5% salt-containing medium, they require biotin for growth, they produce a marked amount of glutamic acid from sugars in high yield and accumulate in medium as shown in examples later described, etc.; and these properties are identical with those of conventionally known glutamic acid producing bacteria. Further in the other morphological properties, physiological and biological properties, the bacteria are common in many properties to known glutamic acid-producing bacteria.

From the foregoing, it is considered that the bacteria of the present invention would reasonably belong to the same genus as that of known glutamic acid-producing bacteria on a genus level. As has been described above, opinion may be divided on in what genus the known glutamic acid-producing bacteria are to be classified but according to the newest Bergey's Manual, 8th edition, in relation to coryneform bacteria group edited with reference to Publications (1) through (10), etc., known glutamic acid-producing bacteria are recited by dividing into the genus Corynebacterium and the genus Brevibacterium. Taking into account that the genus Brevibacterium per se is treated as Genus incertae sidis from a taxonomical viewpoint and the genus Corynebacterium as a regular genus, however, it is considered to be most reasonable at this point of time that the bacteria of the present invention belong to the genus Corynebacterium.

Next, taxonomical examination on a species level is given on the bacteria of the present invention. The following three points in bacteriological properties are different between the bacteria of the present invention and known glutamic acid-producing bacteria in common. A first characteristic point is that the highest temperature showing clearly observable growth is 43° C. or higher. As has been described above, the highest growth temperature of known glutamic acid-producing bacteria is about 42° C. or lower but no bacteria capable of growing at 43° C. or higher exist.

A second characteristic point is resistance to temperature. In resistance to temperature, accurate results can be obtained only with difficulty in the case of performing test in a mass scale using a test tube, etc. because time for thermal conduction and the like greatly vary. Therefore, a test performed by suspending bacteria in skim milk and sealing the suspension in a glass capillary is considered to be best (Publication (3)). The bacteria of the present invention can all survive in skim milk after treatment at 55° C. for 10 minutes by the capillary tube assay method. To the contrary, most of known glutamic acid-producing bacteria are dead after treatment at 55° C. for 10 minutes according to this method; but there is a report that some bacteria show slight survival (Publication (3)).

With respect to this report, the present inventors duplicated the experiment. Test on thermostability was performed with all of the known glutamic acid-producing bacteria shown in Table 1 under the same conditions as in the bacteria of the present invention; as a result, the known glutamic acid-producing bacteria were all dead by treatment at 55° C. for 10 minutes. On the other hand, in the bacteria of the present invention, all of the isolated 14 strains survived by the treatment at 55° C, for 10 minutes. Further 11 out of these strains also survived even by treatment at 60° C. for 10 minutes.

A third characteristic point is that the bacteria of the present invention can accumulate a marked amount of glutamic acid even at 43° C. Conditions for the experiment and amounts of glutamic acid accumulated are as shown in the examples. Accumulation of glutamic acid by the known glutamic acid producing bacteria shown in Table 1 under the same conditions was assayed but all of the bacterial strains did not grow and glutamic acid accumulated was substantially zero.

The properties of the bacteria of the present invention described above are not observed with known glutamic acid-producing bacteria; in particular, it is impossible to raise or improve the properties of the highest growth temperature and thermostability by operation for variation of microorganisms and these properties are considered to be stable. Accordingly, it can be interpreted to have a basis sufficient to consider that the bacteria of the present invention are different from any of the known glutamic acid-producing bacteria. In addition, slight differences in morphological properties such as growth condition, color hue of colonies, etc. and differences in physiological and biochemical properties such as acid formation from sucrose, maltose, trehalose, D-mannitol, inositol, etc., MR test, VP test, nitrate reduction and urease test, etc. are noted between the isolated 14 strains of the present invention. These differences are on a strain level but considered to be inadequate for classifying them into different species. Thus, the bacteria of the present invention were all identified to belong to the same species.

Survey was made by comparing the bacteria of the present invention with bacteria belonging to coryneform bacteria group other than glutamic acid-producing bacteria; however, no bacteria in the corresponding species was found. From the foregoing, the bacteria of the present invention were all identified to be novel species belonging to the genus Corynebacterium and named *Corynebacterium thermoaminogenes* nov. sp. Representative strains belonging to this species are AJ 12308, AJ 12309, AJ 12310 and AJ 12340, which have been deposited as FERM P-9244, FERM BP-1540, FERM P-9245 (FERM BP-1541), FERM P-9246 (FERM BP-1542) and FERM P-9277 (FERM BP-1539) respectively.

These strains identified above by FERM P-9244, 9245, 9246 and 9277 were originally deposited on Mar. 10, 1987 (FERM P-9244-9246) and Mar. 13, 1987 (FERM P-9277) at the Fermentation Research Institute, Agency of Industrial and Technology, Ministry of International Trade and Industry (FHI), 1-3, Higashi 1-chome, Yatabemachi, Tsukuba-gun, Ibaragi-ken 305, Japan, and were accorded the FERM P-9244, 9245, 9246 and 9277 indicated above.

These strains deposits were then converted into deposits under the Budapest Treaty on Oct. 27, 1987. And strains of FERM P-9244, P-9245, P-9246 and P-9277 were accorded the corresponding FERM BP-1540, 1541, 1542 and 1539, respectively.

EXAMPLE 1

In a small fermenter having a volume of 1 liter was charged 300 ml of culture liquid having a medium composition shown in Table 2 and, *Corynebacterium thermoaminogenes* AJ 12308 was cultured at a temperature of 43° C., while appropriately supplementing ammonia gas to keep pH of the culture liquid at 7.5 to 8.0. Five hours after the initiation of the culture, penicilline was added in a concentration of 3 U/ml when nephelometry reached 0.6 and culture was further continued. The culture solution obtained after incubation for 16 hours was analyzed by high performance liquid chromatography. As a result, glutamic acid was accumulated in a concentration of 39.1 g/l. An amount of glutamic acid accumulated was 0.1 g/l or lower in a run simultaneously performed using *Brevibacterium flavum* ATCC 13826 under the same conditions.

TABLE 2

| Composition of Medium Used in Glutamic Acid Fermentation Test | |
| --- | --- |
| Glucose | 100 g |
| Soybean hydrolysate (as total nitrogen) | 0.36 g |
| $KH_2PO_4$ | 1 g |
| $MgSO_4 \cdot 7H_2O$ | 1 g |
| $Fe^{++}$ $Mn^{++}$ | 2m g each |
| Vitamin $B_1 \cdot HCl$ | 100 γ |
| Biotin | 100 γ |
| Ammonium sulfate | 5 g |
| Water | 1,000 ml | pH 7.8

EXAMPLE 2

Glutamic acid fermentation was carried out using *Corynebacterium thermoaminogenes* AJ 12309 in a manner similar to Example 1. As a result, 40.0 g/l of glutamic acid was accumulated in the culture solution obtained after incubation for 19 hours.

EXAMPLE 3

Glutamic acid fermentation was carried out using *Corynebacterium thermoaminogenes* AJ 12310 in a manner similar to Example 1. As a result, 35.2 g/l of glutamic acid was accumulated in the culture solution obtained after incubation for 17 hours.

EXAMPLE 4

Glutamic acid fermentation was carried out using *Corynebacterium thermoaminogenes* AJ 12340 in a manner similar to Example 1. As a result, 38.1 g/l of glutamic acid was accumulated in the culture solution obtained after incubation for 18 hours.

EXAMPLE 5

In a small fermenter having a volume of 1 liter was charged 300 ml of culture liquid having a medium composition shown in Table 2 from which glucose and ammonium sulfate were removed and to which 20 g of ammonium acetate was supplemented and, *Corynebacterium thermoaminogenes* AJ 12308 was cultured at a temperature of 40° C., while appropriately supplementing acetic acid or ammonia gas to keep pH of the culture liquid at 7.5 to 8.0. Eight hours after the initiation of the culture, penicilline was added in a concentration of 3 U/ml when nephelometry reached 0.6 and culture was further continued. The culture solution obtained after incubation for 24 hours was analyzed by high performance liquid chromatography. As a result, glutamic acid was accumulated in a concentration of 32 g/l, which corresponded to yield of 31.5% based on acetic acid.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A biologically pure culture of a *Corynebacterium thermoaminogenes* selected from the group consisting of FERM BP-1539, FERM BP-1540, FERM BP-1541, and FERM BP-1542.

* * * * *

UNITED STATES PATENT AND TRADEMARK OFFICE
CERTIFICATE OF CORRECTION

PATENT NO. : 5,250,434
DATED : October 5, 1993
INVENTOR(S) : Yamada et al

It is certified that error appears in the above-indentified patent and that said Letters Patent is hereby corrected as shown below:

Column 2, line 9 "Bergey's Mannual" should read
--Bergey's Manual--.

Column 3-4, Table 1 Column AJ, 12308, "(1.0-4.0))" should read--
(1.0-4.0)--.

Column 11, line 6 "(as total nitrogen" should read
--(as total nitrogen)--.

Signed and Sealed this

Twentieth Day of December, 1994

Attest:

BRUCE LEHMAN

Attesting Officer          Commissioner of Patents and Trademarks